United States Patent [19]

Reiche

[11] Patent Number: 5,170,794
[45] Date of Patent: Dec. 15, 1992

[54] METHOD AND APPARATUS FOR DERIVING A RESPIRATION SIGNAL AND/OR ARTIFACT SIGNAL FROM A PHYSIOLOGICAL SIGNAL

[75] Inventor: Martin Reiche, Holderweg, Fed. Rep. of Germany

[73] Assignee: Hewlett-Packard Company, Palo Alto, Calif.

[21] Appl. No.: 644,501

[22] Filed: Jan. 23, 1991

[51] Int. Cl.⁵ .............................................. A61B 5/08
[52] U.S. Cl. .................................... 128/671; 128/696; 128/723; 128/734
[58] Field of Search ............... 128/671, 700, 716, 720, 128/723, 734

[56] References Cited

U.S. PATENT DOCUMENTS

| | | | |
|---|---|---|---|
| 3,608,542 | 9/1971 | Pacela et al. | 128/723 |
| 3,976,052 | 8/1976 | Junginger et al. | 128/723 |
| 4,379,460 | 4/1983 | Judell | 128/723 |
| 4,422,458 | 12/1983 | Kravath | 128/671 |
| 4,582,068 | 4/1986 | Phillipps et al. | 128/716 |
| 4,781,201 | 11/1988 | Wright et al. | 128/723 |

OTHER PUBLICATIONS

"Methods of filtering the heart-beat artifact from the breathing waveform of infants obtained by impedance pneumography," Wilson et al, *Medical & Biological Engineering & Computing*, May 1982.

Primary Examiner—Ruth S. Smith
Assistant Examiner—Robert L. Nasser, Jr.

[57] ABSTRACT

A method for deriving a respiration signal and/or a cardiac artifact signal from a physiological signal, in particular an impedance pneumography signal, includes detection of a heartbeat moment, storing the amplitude of the physiological signal at the heartbeat moment, and calculating and storing a learning signal, the learning signal being a function of a previous learning signal and the difference between the instantaneous amplitude of the physiological signal and the stored amplitude thereof. The learning signal is either read out starting each time with the particular heartbeat moment, for deriving the cardiac artifact signal, or subtracted from the physiological signal at each heartbeat moment for deriving the respiration signal.

13 Claims, 3 Drawing Sheets

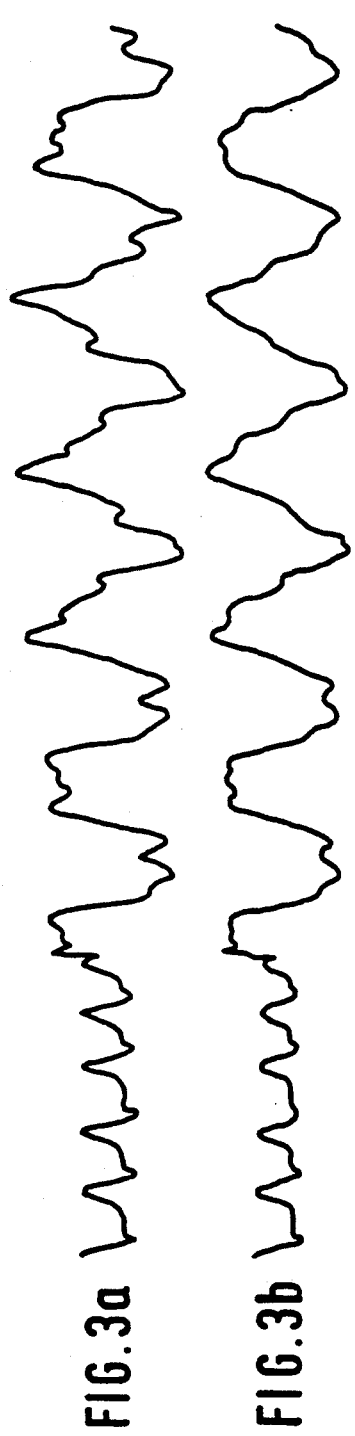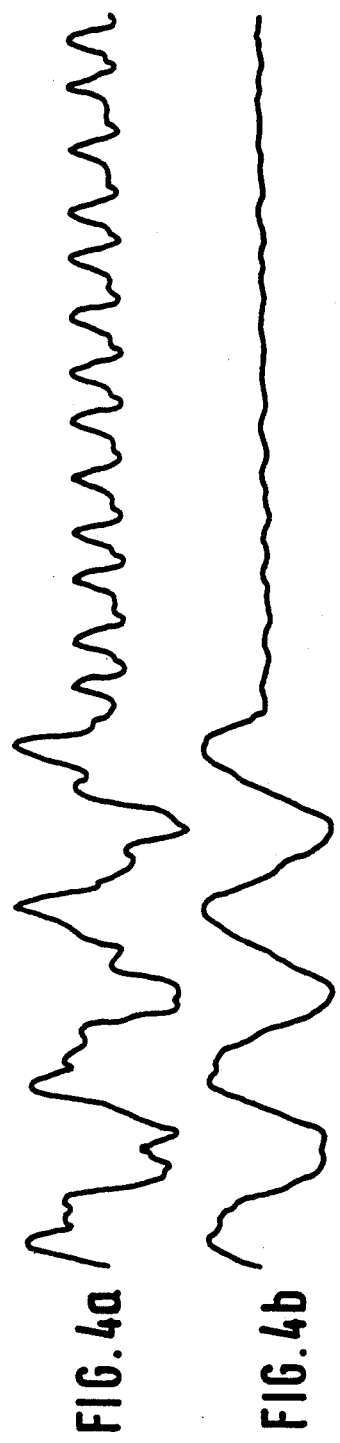
FIG.3a  FIG.3b  FIG.4a  FIG.4b

METHOD AND APPARATUS FOR DERIVING A RESPIRATION SIGNAL AND/OR ARTIFACT SIGNAL FROM A PHYSIOLOGICAL SIGNAL

FIELD OF THE INVENTION

The present invention relates to a method of deriving a respiration signal and/or a cardiac artifact signal from a physiological signal having at least a respiration signal component and a cardiac artifact signal component. More particularly, the present invention relates to a method of deriving a respiration signal and/or a cardiac artifact signal from an impedance pneumography signal. Still more particularly, the present invention relates to a method of deriving or producing a respiration signal and/or a cardiac artifact signal on the basis of an impedance pneumography signal detected by means of electrodes placed on the thorax of a patient.

BACKGROUND OF THE INVENTION

Impedance pneumography usually is used in monitoring the respiratory activity of spontaneously breathing patients and employs for signal detection the electrical impedance of the thorax, which impedance is influenced by the patient's respiratory activity and thus changes as a function of time.

It is generally known that an impedance pneumography signal does not only have a respiration signal component, but has additional artifacts superimposed thereon, including a cardiac artifact signal component which indicates the impedance change occurring during the blood flow associated with systole. Additional parameters disturbing the impedance pneumography signal are, for example, spontaneous motion artifacts of the patient. While motion artifacts are difficult to eliminate, there are a number of methods of filtering out the cardiac artifact signal component from an impedance pneumography signal in order to obtain a respiration signal.

For example, European Patent EP-B1-0082655 and related U.S. Pat. Nos. 4,537,196 and 4,582,068 disclose a method of processing a physiological signal (which signal may be an impedance pneumography signal) wherein the cardiac artifact signal masking the respiration signal is assumed to be periodic so that, for calculation of a filtered signal, the artifact frequency, which is assumed to be constant, is ascertained at first and thereafter a signal of the particular frequency in the impedance pneumography signal is suppressed in a digital filter to produce the filtered signal. This known method requires a threshold detection circuit for determining a threshold value as a function of preceding levels of previously filtered impedance pneumography signals. The threshold detection circuit is fed with the filtered impedance pneumography signal in order to produce a periodic signal indicating recurrence of the respiration signal when the filtered functional signal exceeds the threshold value of the threshold detection circuit. This known filtering technique is capable of suppressing only the basic component of a cardiovascular artifact occurring with a fixed periodicity. However, the requirement of maintaining periodicity of the disturbing signal is not met in most practical situations; therefore, the results obtained by this known method are unsatisfactory.

EP-A2-0048591 discloses a further filtering technique for obtaining a respiration signal from an impedance pneumography signal by filtering out a cardiac masking signal. According to this known method the heart rate is measured by means of an electrocardiograph to determine the heartbeat period which is used for delaying the impedance signal on the input side by one heartbeat period and for subtracting this signal thereafter from the impedance signal. This known filtering technique is also inadequate when the cardiovascular artifact is not sufficiently periodic.

W089/01312 discloses a method of processing impedance signals which includes filtering out a respiration signal component from the signal representing the impedance of the thorax. For suppressing the stronger impedance change of the thorax due to respiration as compared to the impedance change due to heart activity, a clamping circuit is activated in synchronization with the heart activity at a moment of time before the beginning of the mechanical systole. This circuit is only opened during the duration of the mechanical systole so that the output signal represents only the voltage fluctuation due to the mechanical systole. However, in nature the cardiovascular signal is masked by a slight respiration signal component during this period of time as well, thus making this filtering technique inaccurate.

U.S. Pat. No. 3,976,052 reveals a method of deriving a respiration signal from an impedance pneumography signal by filtering out a cardiac artifact signal, in which the heart rate is measured and the period of the heartbeat is compared to the period of the impedance pneumography signals. When the periods of both signals are essentially identical, i.e., when the impedance pneumography signals are caused by the heartbeat, a carrier threshold value is increased to such an extent that further response to signals caused by heartbeat is prevented. Thus, after this automatic basic adjustment, respiration signals having an amplitude in excess of the amplitude of cardiac artifact signals are automatically detected.

U.S. Pat. No. US-C-3,608,542 discloses a further filtering method for impedance pneumography in which, for suppressing cardiovascular signal components, adjustable narrow-band filters and adjustable level detectors are employed so that good filtering results are provided only if the cardiac artifact signal component to be filtered out is highly periodic.

SUMMARY OF THE INVENTION

In light of the above-described methods, it is the object of the present invention to develop a method of deriving a respiration signal and/or a cardiac artifact signal from a physiological signal having at least a respiration signal component and a cardiac artifact signal component in such a manner that higher accuracy of the respiration signal and/or the cardiac artifact signal derived from the impedance pneumography signal is obtained.

The present invention provides a method of deriving an output signal from a physiological signal having at least a respiration signal component and a cardiac artifact signal component, the output signal being indicative of a respiration signal and/or a cardiac artifact signal. The method comprises the following steps:

First, detecting a heartbeat moment. Next, storing the amplitude of the physiological signal at the time of the heartbeat moment. Next, calculating and storing a learning signal related to the heartbeat moment. The learning signal is calculated as a function of a previous learning signal and the difference between the instantaneous amplitude of the physiological signal and the stored amplitude of the physiological signal. Finally, deriving the output signal from either the instantaneous amplitude or the difference between the instantaneous amplitude and the previous learning signal.

In a most preferred embodiment, the physiological signal detected is an impedance pneumography signal. Moreover, in the most preferred embodiment the step of calculating and storing the learning signal comprises calculating and storing a plurality of learning signal values for a plurality of moments of time. According to the invention, each moment occurs at a predetermined time interval from the heartbeat moment. In addition, in the most preferred embodiment the learning signal is subtracted from the impedance pneumography signal to derive a respiration signal substantially free of cardiac artifact signal components or cardiovascular artifacts.

BRIEF DESCRIPTION OF THE DRAWINGS

FIGS. 3a and 4a show exemplary impedance pneumography signals and FIGS. 3b and 4b show corresponding respiration signals which are largely free of cardiac artifact signal components and which were calculated from the impedance pneumography signals in accordance with the invention.

DETAILED DESCRIPTION OF THE PREFERRED EMBODIMENTS

Figure 1:
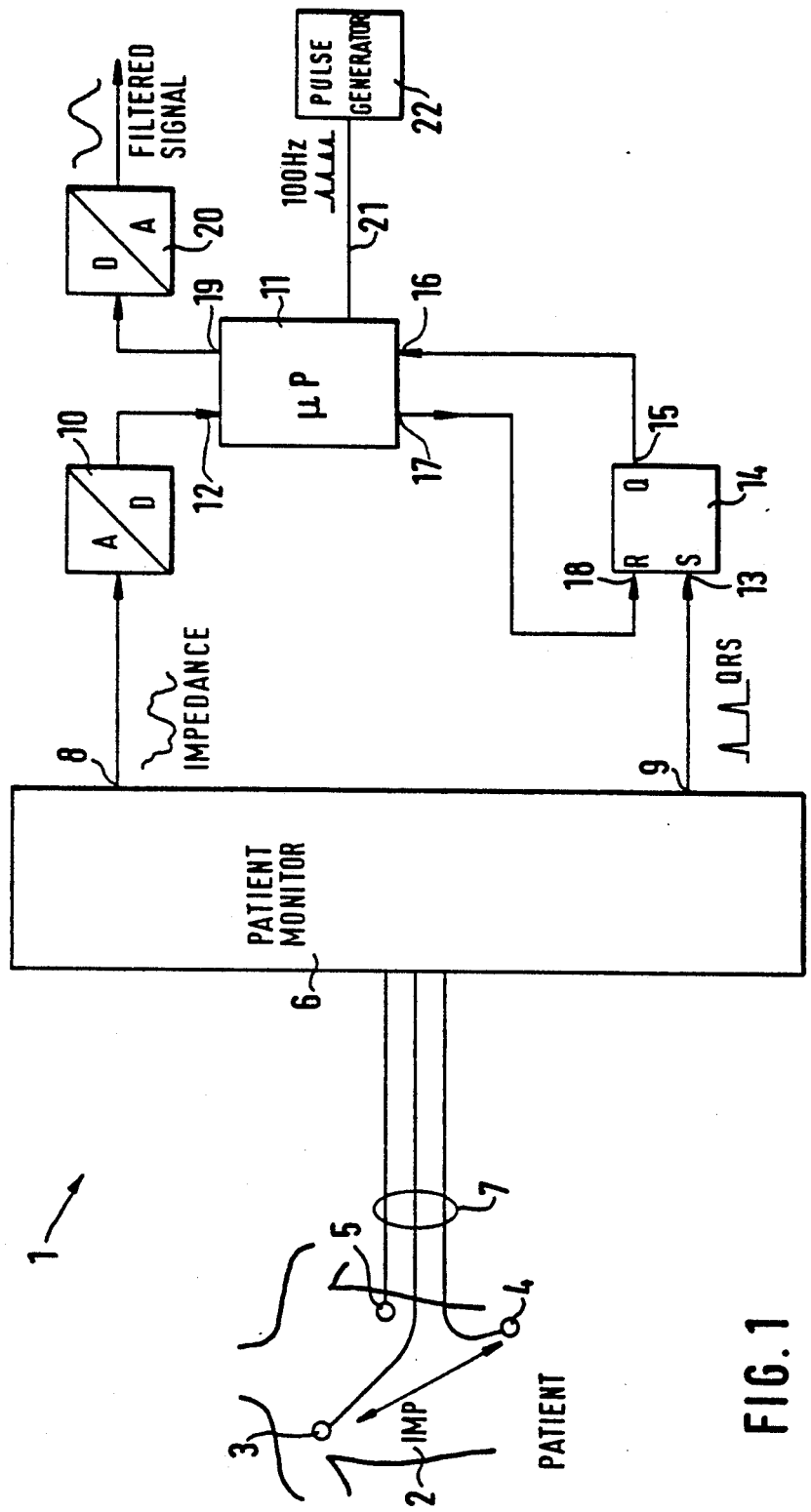
FIG. 1 is a block diagram of an apparatus for deriving a respiration signal from an impedance pneumography signal and a QRS signal in accordance with the present invention.

The invention starts from the realization that a cardiac artifact signal can by no means be assumed to be a signal having a fixed period or a period changing slowly in time, but that it is a signal which, starting from a specific starting point in terms of time within the heartbeat cycle (referred to hereinafter as the "heartbeat moment") has a signal pattern or waveform which remains substantially unchanged from one heartbeat to another heartbeat. The invention simulates this signal pattern by means of an adaptive or learning signal in a self-adaptive routine whereby the heartbeat moment is detected and the amplitude of the physiological signal at this moment is stored as a reference amplitude. Thereafter, the learning signal having a pattern related to the heartbeat moment is calculated and stored on the basis of the difference between the instantaneous amplitude of the physiological signal and the stored amplitude thereof and on the basis of previous learning signals. With a suitable calculation of the learning signals, components of the physiological signal not correlated with the heartbeat moment are reduced, whereas components correlated with the heartbeat moment are increased, so that the learning signal continuously adapts itself to the current cardiac artifact signal component. As is elucidated in more detail below, the learning signal obtained in this way may be used directly as an output signal when the cardiac artifact signal is desired as an output signal, or, by subtraction from the physiological signal, for calculating the respiration signal free of the cardiac artifact signal.

The inventive method allows derivation of the respiration signal and/or cardiac artifact signal by means of a digital circuit, in particular by means of a commercially available microcomputer. The learning signal for this purpose is divided into a plurality of learning signal values so that it can be stored in a semi-conductor memory under a number of addresses corresponding to values of the learning signal taken at different time intervals from the heartbeat moment.

When the method according to the invention is to be employed for deriving or calculating a respiration signal on the basis of an impedance pneumography signal, the respiration signal can be separated from the cardiac artifact signal components by subtracting the learning signal from the impedance pneumography signal.

The inventive method is particularly well suited for being carried out by means of a commercially available microcomputer in which the time value is reset upon occurrence of each heartbeat moment and is then incremented so that it may be used as an access address for reading out as well as for storing the particular learning signal values.

New learning signal values can be derived by means of a simple rule from previous learning signal values taken at corresponding times in the heartbeat cycle and the difference between the instantaneous amplitude and the stored amplitude of the physiological signal. By weighting of the former learning signal values and the difference, a learning function is achieved, which function results in a learning signal simulating the cardiac artifact signal, with the cardiac artifact signal detected last contributing most to the learning signal and the cardiac artifact signals detected therebefore contributing to a lesser and lesser degree in accordance with their remoteness. This learning function results in continuous adaptation of the learning signal to the cardiac artifact signal, eliminates signal components not related to the heartbeat moment by time averaging, and increasingly eliminates the effects of cardiac artifact signals occurring further back in time.

The heartbeat moment can be derived preferably from an electrocardiograph through the pulse of a QRS signal. This way of determining the heartbeat moment is an expedient since the QRS signal is a parameter that is already present in usual patient monitors. It should be noted that the term "heartbeat moment" as used herein means any reference point within a cardiac artifact signal.

It is also noted that cardiovascular artifacts or cardiac artifact signals have a limited amplitude whose maximum value is typically less than 0.5 Ohm. In the case of weak respiration, the respiration signal amplitude is typically on the order of 1 ohm. During impedance pneumography monitoring of newborn babies the extreme situation may occur that the respiratory rate is identical to the heart rate. By limiting the amplitude of the learning signal, a situation is prevented wherein the respiration signals are made zero by erroneous integration thereof in the learning signal due to the identical rates of the signals, so that safe respiration signal detection is ensured.

Next, a preferred embodiment of an apparatus according to the invention, operating in accordance with the inventive method, is described with reference to the drawings, wherein like numerals and like reference characters designate like elements or steps.

Referring now to FIG. 1, an apparatus suitable for carrying out the inventive method, and designated with the reference numeral 1, comprises two impedance measuring electrodes 3, 4 placed on the thorax of a patient for determining the thorax impedance therebetween and deriving an impedance pneumography signal, as well as an ECG electrode 5 for producing an electrocardiography signal. The signals mentioned are supplied to a patient monitor 6 via a three-wire electrode-patient cable 7. The patient monitor is preferably a monitor of the type designated as "Hewlett-Packard 78354." The monitor 6 produces on its output side an impedance pneumography signal on a first output 8 as well as a QRS signal, which is representative of the heartbeat moment and derived from the ECG signal, on a second output 9.

The apparatus for obtaining the impedance pneumography signal and the QRS signal is known from the prior art and therefore need not be described in detail.

The impedance pneumography signal from the first output 8 is converted by an A/D converter 10 to a digital signal that is fed to a microcomputer 11 on a first input port 12 thereof. The pulse-like QRS signal from the second output 9 of the patient monitor 6 is fed to the setting input 13 of an RS-flip-flop 14. A Q-output 15 of RS-flip-flop 14 is connected to a second input port 16 of microcomputer 11. As soon as the microcomputer 11 has detected the presence of a high logical level at its second input port 16, which is caused by a preceding QRS pulse, the microcomputer 11 generates at its first output 17 a resetting signal which is fed to the resetting input 18 of the RS-flip-flop 14. As will be apparent to those skilled in the art, the RS-flip-flop 14 serves to ensure safe detection of a pulse of the QRS signal by the microcomputer 11. The filtered respiration signal is produced by the microcomputer at a second output port 19 connected to a D/A converter 20.

A pulse generator 22 feeds its signal into an interrupt line 21 of processor 11, thus causing the continuous repetition of the execution of the program described below with reference to FIG. 2. The preferred execution frequency is about 100 Hz.

Figure 2:
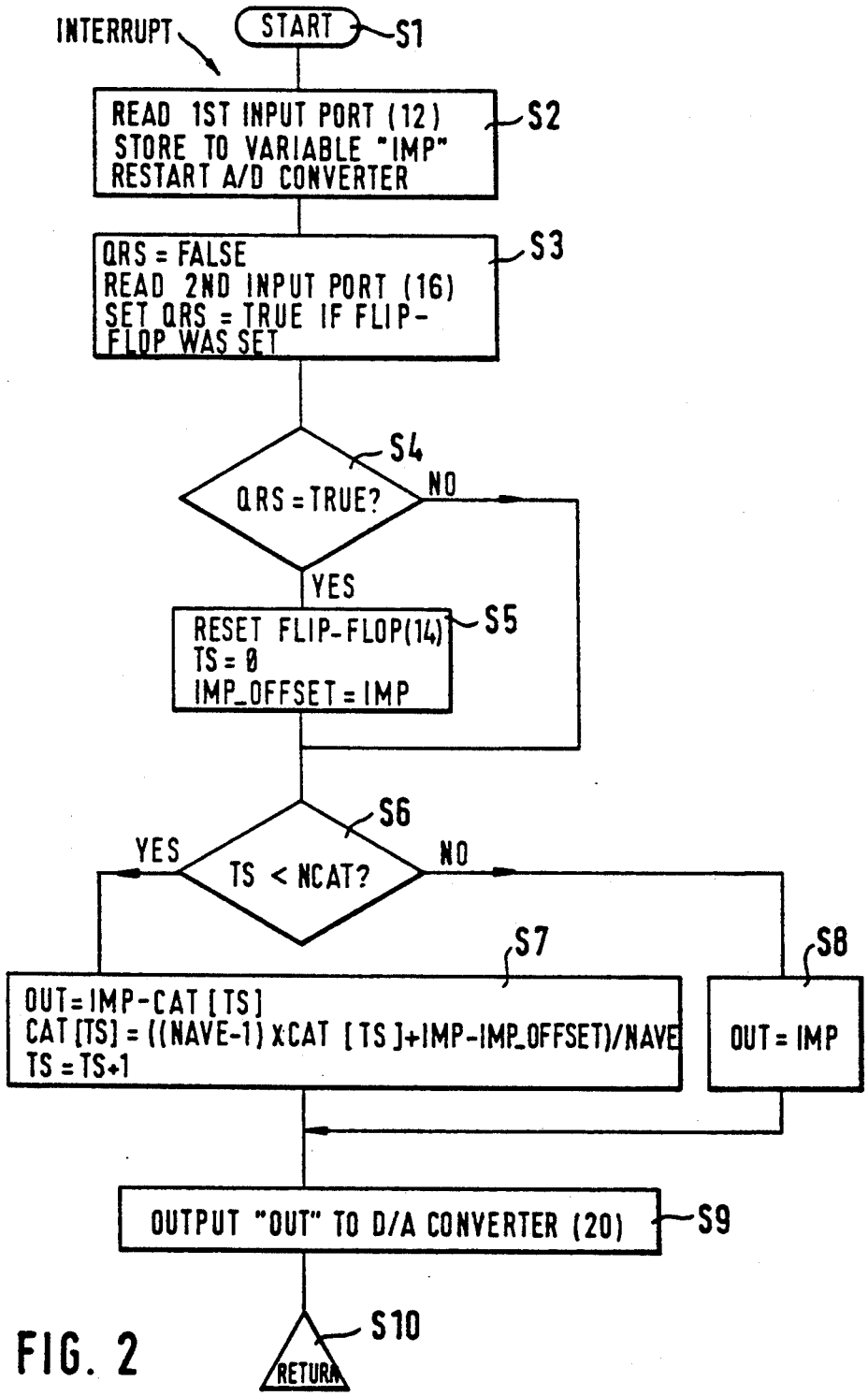
FIG. 2 is a flow diagram of a method for operating the microcomputer of FIG. 1 to derive a respiration signal from an impedance pneumography signal and a QRS signal in accordance with the present invention.

Next, a flow diagram of the program will be elucidated with reference to FIG. 2, indicating the operation of microcomputer 11 for carrying out the inventive method of calculating a filtered respiration signal from an impedance pneumography signal. Subsequent to receiving an interrupt signal (21, FIG. 1) at step S1, microcomputer 11 reads the impedance value present at its first input port 12, stores the same as a variable "IMP" and effects restarting of A/D converter 10 in the second program step S2.

In the third program step S3 the logical value QRS, which is representative of the presence or absence of a QRS pulse, is initialized to the value "FALSE". The logical value issued from the output of flip-flop 14 and present at the second input port 16 is read in. As soon as the flip-flop is set the logical value QRS is set to "TRUE".

It is determined in the fourth program step S4 whether the logical value QRS is "TRUE". If so, the program continues with a fifth program step S5. Otherwise, the programs jumps to a sixth program step S6.

In the fifth program step the flip-flop 14 is reset by producing logic high level at the first output 17 of the microcomputer, and a value TS representing the time axis is set to zero. The amplitude value IMP of the impedance pneumography signal present at this reference time is stored as a reference amplitude IMP_OFFSET.

In the sixth program step S6 it is determined whether the instantaneous time value TS is smaller than a maximum value NCAT representative of the maximum duration of the learning signal starting from the occurrence of the heartbeat moment (TS=0). If so, the program proceeds with a seventh program step S7, whereas it otherwise continues with an eighth program step S8.

In the seventh program step S7 the output signal OUT of the microcomputer is first set to the difference between the instantaneous impedance value IMP and the learning signal value CAT(TS) associated with the instantaneous time value TS.

In a subsequent step a new learning signal value CAT(TS) is set by multiplying the former learning signal value CAT(TS) by an averaging constant NAVE reduced by 1, and this value is increased by the difference between the instantaneous amplitude and the stored reference amplitude (IMP_ IMP_OFFSET), and the resulting quantity is divided by the averaging constant NAVE. Thereafter the instantaneous time value TS is incremented by 1.

If the result of the determination made in sixth program step S6 is negative, the output value OUT is set in the eighth program step S8 to the instantaneous value of the impedance pneumography signal IMP since in this case no correction thereof has to be carried out.

In the ninth program step S9 the output value OUT is supplied to the D/A converter 20 as a filtered output signal which is issued by the converter in analog form. After step S9, the processor waits for a new interrupt at step S10 before returning to the fourth program step S4.

FIGS. 3a and 4a (FIG. 4a is a continuation of FIG. 3a) show a pattern of a pneumography signal which was artificially simulated. FIGS. 3b and 4b the show output signal curve calculated in accordance with the inventive method, with the above-described routine used for the calculation. For a better understanding of the curves, it should be noted that the learning signal values "CAT(TS)" were set to zero at the beginning of the particular calculation routines. As the learning process proceeds, which can be observed on the basis of the output curves of FIGS. 3b, 4b, the disturbing component in the input signal, which corresponds to the cardiac artifact signal component, is suppressed in increasing manner such that the filtered signal corresponds to a pure respiration signal. The operability of the method according to the invention was tested using the inventive algorithm together with patient signals. The operability can also be proved upon occurrence of ventricular extrasystoles at an irregular heart rate and in case of erroneous QRS determinations.

Although specific embodiments have been described, the true scope of the invention is not limited thereto. For example, although the inventive method as described is used only for obtaining a respiration signal free of cardiac artifact signal components on the basis of an impedance pneumography signal, it will be recognized by those skilled in the art that it may also be used for producing a cardiac artifact signal free of respiration signal components, or for producing both signals simultaneously. Accordingly, the invention is intended to be limited only by the following claims.

What is claimed is:

1. A method of deriving an output signal from a physiological signal having at least a respiration signal component and a cardiac artifact signal component, said output signal indicative of a respiration signal and/or a cardiac artifact signal, the method comprising the steps of:

(a) detecting a heartbeat moment;

(b) measuring and storing the amplitude of a signal with an impedance pneumograph at approximately the time of said heartbeat moment;

(c) measuring an instantaneous amplitude of said signal at a time after the time of the heartbeat moment;

(d) calculating the difference between the instantaneous amplitude of the signal and the stored amplitude thereof;

(e) calculating and storing a learning signal related to the heartbeat moment, said learning signal calculated as a function of a previous learning signal and the difference between the instantaneous amplitude of the signal and the stored amplitude thereof; and (f) performing at least one of the following steps:

(f1) generating an output signal indicative of a cardiac artifact signal by reading out said learning signal, and (f2) calculating the difference between the instantaneous amplitude of the signal and the learning signal, and generating an output signal indicative of a respiration signal from said difference between the instantaneous amplitude of the signal and the learning signal.

2. The method recited in claim 1, comprising measuring an impedance pneumography signal.

3. The method recited in claim 2, wherein the step of calculating and storing the learning signal comprises calculating and storing a plurality of learning signal values for a plurality of moments of time, each moment occurring a predetermined time interval from the heartbeat moment.

4. The method recited in claim 3, comprising subtracting the learning signal from the impedance pneumography signal and thereby deriving a respiration signal substantially free of cardiac artifact signal components or cardiovascular artifacts.

5. The method recited in claim 4, further comprising the steps of, for each heartbeat cycle starting with a heartbeat moment, incrementing a time value (TS) starting from the heartbeat moment, accessing a learning signal value CAT(TS) corresponding to a particular instant of time and subtracting said learning signal value CAT(TS) during said heartbeat cycle from the instantaneous impedance pneumography signal.

6. The method recited in claim 5, comprising the step of calculating a new learning signal value associated with a particular length of time from the heartbeat moment from a previous learning signal value associated with the particular length of time and from the instantaneous difference between the instantaneous amplitude and the stored amplitude of the physiological signal by multiplying the former learning signal value CAT(TS) by an averaging constant (NAVE) reduced by 1, increasing this value by the difference between the instantaneous amplitude and the stored amplitude of the physiological signal and dividing the resulting quantity by the averaging constant NAVE.

7. The method recited in claim 6, comprising the step of deriving the heartbeat moment from an electrocardiograph and the pulse of a QRS signal.

8. The method recited in claim 7, comprising the step of limiting the learning signal value to a maximum value which is lower than a usual respiration signal amplitude.

9. The method recited in claim 8, comprising limiting the maximum value of the learning signal value to 1 Ohm.

10. The method recited in claim 9, comprising reading out the learning signal periodically starting with each heartbeat moment for deriving a cardiac artifact signal free of respiration signal components.

11. An apparatus for deriving an output signal from a physiological signal having at least a respiration signal component and a cardiac artifact signal component, said output signal indicative of a respiration signal and/or a cardiac artifact signal, said apparatus comprising:

(a) means for detecting a heartbeat moment;

(b) an impedance pneumograph means for measuring and storing the amplitude of a signal at approximately the time of said heartbeat moment;

(c) means for measuring an instantaneous amplitude of said signal at a time after the time of the heartbeat moment;

(d) means for calculating the difference between the instantaneous amplitude of the signal and the stored amplitude thereof;

(e) means for calculating and storing a learning signal related to the heartbeat moment, said learning signal calculated as a function of a previous learning signal and the difference between the instantaneous amplitude of the signal and the stored amplitude thereof; and (f) means for deriving said output signal, including means for reading out said learning signal and means for calculating the difference between the instantaneous amplitude of the signal and the learning signal and deriving the output signal from said difference between the instantaneous amplitude of the signal and the learning signal.

12. A system for deriving an output signal from a physiological signal having at least a respiration signal component and a cardiac artifact signal component, said output signal indicative of a respiration signal and/or a cardiac artifact signal, said apparatus comprising:

(a) monitor means for measuring a physiological condition of a patient and generating a physiological signal on the basis of said physiological condition, and for detecting a heartbeat moment and EKG means for providing a QRS signal indicative of said heartbeat moment;

(b) A/D means coupled to said monitor means for digitalizing said physiological signal;

(c) means, coupled to said A/D means, for storing the amplitude of the digitalized physiological signal at approximately the time of said heartbeat moment;

(d) means for calculating and storing a learning signal related to the heartbeat moment, including means for calculating the difference between the instantaneous amplitude of the physiological signal and the stored amplitude thereof and for calculating said learning signal as a function of a previous learning signal and the difference between the instantaneous amplitude of the physiological signal and the stored amplitude thereof; and (e) means for deriving said output signal, including means for reading out said learning signal and means for calculating the difference between the instantaneous amplitude of the physiological signal and the learning signal.

13. The system recited in claim 12, wherein said monitor means comprises means for generating an impedance pneumography signal.

* * * * *

UNITED STATES PATENT AND TRADEMARK OFFICE
CERTIFICATE OF CORRECTION

PATENT NO. : 5,170,794
DATED : December 15, 1992
INVENTOR(S) : Martin Reiche

It is certified that error appears in the above-indentified patent and that said Letters Patent is hereby corrected as shown below:

Column 2, line 23, change "Pat. No." to --US-C- --.

Column 2, line 38, delete "U.S. Patent No.".

Signed and Sealed this

Twenty-eighth Day of June, 1994

Attest:

BRUCE LEHMAN

Attesting Officer      Commissioner of Patents and Trademarks